US007089681B2

(12) United States Patent
Herbert et al.

(10) Patent No.: US 7,089,681 B2
(45) Date of Patent: Aug. 15, 2006

(54) METHOD AND APPARATUS FOR FILTERING AND DRYING A PRODUCT

(75) Inventors: Paul F. Herbert, Wayland, MA (US); Douglas M. Bissonnette, Ashland, MA (US); Gregory C. Troiano, Weymouth, MA (US)

(73) Assignee: Alkermes Controlled Therapeutics, Inc., Cambridge, MA (US)

( * ) Notice: Subject to any disclaimer, the term of this patent is extended or adjusted under 35 U.S.C. 154(b) by 239 days.

(21) Appl. No.: 10/304,058

(22) Filed: Nov. 26, 2002

(65) Prior Publication Data

US 2004/0099612 A1    May 27, 2004

(51) Int. Cl.
*B03C 3/00*   (2006.01)

(52) U.S. Cl. ............... 34/92; 34/165; 34/168; 34/177; 34/202; 34/540; 34/589; 34/282; 62/440; 62/441; 62/442; 62/443; 62/444; 62/445; 62/446; 95/74; 118/723; 210/181; 210/184; 210/175; 210/406; 210/723; 210/767; 210/774; 426/384

(58) Field of Classification Search ............... 210/406, 210/181, 184, 175, 767, 774; 34/540, 589, 34/165, 168, 177, 92, 202, 282; 118/723; 95/74; 426/384; 62/440–446
See application file for complete search history.

(56) References Cited

U.S. PATENT DOCUMENTS

| | | | |
|---|---|---|---|
| 3,672,068 A * | 6/1972 | Wilkison | 34/412 |
| 3,731,392 A | 5/1973 | Gottfried | |
| 4,015,341 A * | 4/1977 | McKinney et al. | 34/263 |
| 4,142,873 A * | 3/1979 | Berz | 95/74 |
| 4,229,886 A * | 10/1980 | Durant | 34/92 |
| 4,583,301 A * | 4/1986 | Crowley et al. | 34/73 |

(Continued)

FOREIGN PATENT DOCUMENTS

EP    0 000 181 A1    1/1979

(Continued)

OTHER PUBLICATIONS

Basic Industrial Freezer Dryer (Apr. 30, 2002), at http://www.rpi.edu/dept/chem-eng/Biotech-Environ/LYO/Fig.7.html.

(Continued)

*Primary Examiner*—Duane Smith
*Assistant Examiner*—Minh-Chau T. Pham
(74) *Attorney, Agent, or Firm*—Andrea G. Reister; Covington & Burling

(57) ABSTRACT

The present invention relates to a method and apparatus for filtering and drying a product. In a preferred embodiment, the apparatus comprises a container having a plurality of porous walls and a plurality of solid walls that divide the container into a plurality of product chambers, a plurality of vacuum chambers, and, preferably, a plurality of heat transfer chambers. Each product chamber shares at least one porous wall with an adjacent vacuum chamber. Each product chamber preferably shares at least one solid wall with an adjacent heat transfer chamber. According to the method of the present invention, a product is introduced into the product chambers, where the product is held while a substance is filtered from the product through the porous walls and the product is dried by reducing the pressure in the vacuum chambers and the product chambers. In a preferred embodiment of the method, a heat transfer fluid flows through the heat transfer chambers to facilitate keeping the product frozen and/or to facilitate faster drying of the product.

55 Claims, 7 Drawing Sheets

U.S. PATENT DOCUMENTS

| | | | | |
|---|---|---|---|---|
| 4,746,432 A | * | 5/1988 | Taki et al. | 210/493.5 |
| 5,019,400 A | | 5/1991 | Gombotz et al. | |
| 5,426,864 A | * | 6/1995 | Svehaug et al. | 34/70 |
| 5,428,905 A | | 7/1995 | Beurel et al. | |
| 5,884,414 A | | 3/1999 | Anger | |
| 5,993,674 A | * | 11/1999 | Rolchigo et al. | 210/780 |
| 6,117,322 A | * | 9/2000 | Miller et al. | 210/321.63 |
| 6,148,536 A | | 11/2000 | Iijima | |
| 6,202,319 B1 | * | 3/2001 | Bening | 34/165 |
| 6,261,518 B1 | * | 7/2001 | Caputo et al. | 422/22 |
| 6,367,412 B1 | * | 4/2002 | Ramaswamy et al. | 118/723 I |
| 2003/0115768 A1 | * | 6/2003 | Hoffman | 34/92 |
| 2004/0159616 A1 | * | 8/2004 | Cohee et al. | 210/767 |

FOREIGN PATENT DOCUMENTS

| | | |
|---|---|---|
| JP | 59169504 | 9/1984 |

OTHER PUBLICATIONS

Freeze Dryer with Shelf (Apr. 30, 2002), at http://www.rpi.edu/dept/chem.eng/Biotech-Environ/LYO/Fig.6.html.

Principles of Lyophiliation Equipment (Apr. 30, 2002), at http://www.rpi.edu/dept/chem-eng/Biotech-Environ/LYO/Section3.html.

Schematic of a Laboratory Freeze Dryer with Shell Frozen Flasks Attached to a Manifold (Apr. 30, 2002), at http://www.rpi.edu/dept/chem-eng/Biotech-Environ/LYO/Fig.5.html.

Suppression of Frothing by Centrifugation (Apr. 30, 2002), at http://www.rpi-edu/dept/chem-eng/Biotech-Environ/LYO/Fig.4.html.

Ultrasimple Freeze Dryer (Apr. 30, 2002), at http://rpi.edu/dept/chem.eng/Biotech-Environ/LYO/Fig.3.html.

* cited by examiner

METHOD AND APPARATUS FOR FILTERING AND DRYING A PRODUCT

BACKGROUND OF THE INVENTION

1. Field of the Invention

The present invention relates to a method and apparatus for filtering and drying a product. In a preferred embodiment, the present invention relates to a method and apparatus for filtering and freeze drying a frozen suspension in order to make a freeze dried powder suitable for use as a medicament.

2. Related Art

It is often desirable to filter and dry a product as part of a manufacturing process. For example, in the pharmaceutical field, it is often desirable to filter and freeze dry a frozen suspension of a drug into a dry, inhalable powder or a dry, friable powder. For example, the well known powder production process (PPP)—described in U.S. Pat. No. 6,284,283, the entirety of which is incorporated herein by reference—yields a suspension of atomized frozen protein particles suspended in liquid nitrogen ($LN_2$) that must be filtered and dried to form a dry, inhalable powder.

In one known method for filtering and drying a drug suspended in liquid nitrogen, the suspension is transferred into porous polyester bags, wherein the liquid nitrogen is evaporated and filtered, leaving only the drug particles. The drug particles are then freeze dried by placing the bags inside a drying chamber of a conventional shelf freeze dryer (also known as a lyophilizer). In the drying chamber of a conventional shelf freeze dryer, the bags rest upon shelves that are able to be heated or cooled in order to facilitate the freeze drying. When the chamber door is closed, a vacuum pump can be actuated to reduce the pressure in the chamber, which freeze dries the product by causing the moisture to sublime. While the pressure is being reduced, the shelves are heated, which facilitates drying of the product. After drying is complete, the vacuum is relieved and the door to the chamber opened. The bags are removed from the chamber and the freeze dried drug powder is harvested from the bags by inverting each bag over another container.

This known method and apparatus for filtering and drying a product suffers from several drawbacks. First, the product must be filtered and freeze dried in separate containers, necessitating transfer of the product to the freeze drier in order to dry it. In addition, the freeze dryer requires the use of secondary containers (i.e., bags) inside of the drying chamber. Also, in the shelf freeze drier, the heat source (i.e., heat transfer fluid inside the shelf) is not located a uniform distance from the product, which may result in uneven or incomplete freeze drying. Further, the transfer of the product from bags to a jar can result in product loss.

Other known freeze dryers also suffer from drawbacks. For example, U.S. Pat. No. 5,884,414 discloses a freeze dryer in which the product to be dried is placed directly into the drying chamber. However, this dryer does not have the ability to filter the product and does not have a heat transfer source for heating or cooling the product. U.S. Pat. No. 3,731,392 discloses a freeze dryer, in which the product to be dried is freeze dried in multiple, continuous drying chambers. However, this dryer does not have the ability to filter the product.

Thus, there is a need in the art for an improved method and apparatus for filtering and drying a product. What is needed is a method and apparatus that allows a product to be filtered and dried in a single container, without necessitating the use of secondary containers. What is also needed is a method and apparatus in which the heat transfer source and the vacuum source remain close to the product, to better penetrate a product for more uniform and efficient drying. In addition, what is needed is a method and apparatus that allows for direct harvesting of the product from the container holding the product to avoid spillage and waste of product. Such an apparatus also would have a compact shape and design to be convenient for use. The present invention, which is fully set forth below, fulfills these and other needs for an improved method and apparatus for filtering and drying a product.

SUMMARY OF THE INVENTION

The present invention relates to an apparatus for filtering and drying a product. According to an embodiment of the present invention, the apparatus comprises a product chamber and a vacuum chamber that share a porous wall. The product chamber is configured to hold the product to be filtered and dried. A substance can be filtered from the product through the porous wall and the product can be dried by reducing the pressure in the vacuum chamber and in the product chamber.

According to another embodiment of the present invention, the apparatus for filtering and drying a product comprises a container that contains a plurality of porous walls and a plurality of solid walls that divide the container into a plurality of product chambers, a plurality of vacuum chambers, and, preferably, a plurality of heat transfer chambers. Each product chamber shares at least one porous wall with an adjacent vacuum chamber. Each product chamber preferably shares at least one solid wall with an adjacent heat transfer chamber. The product chambers are configured to hold the product while a substance is filtered from the product through the porous walls and the product is dried by reducing the pressure in the vacuum chambers and the product chambers.

The apparatus preferably further comprises a vacuum coupled to and in communication with the vacuum chambers. The vacuum preferably comprises a vacuum pump and a condenser that are coupled to the vacuum chambers. The vacuum pump can be actuated to reduce the pressure in each vacuum chamber and in each product chamber, which dries the product by causing the moisture in the product to evaporate or sublime and be frozen and condensed inside of the condenser. If the product is frozen and the vacuum pressure is low enough, the product can be freeze dried.

Each heat transfer chamber preferably comprises a heat transfer inlet and a heat transfer outlet, so that a heat transfer fluid can flow through the heat transfer chambers in order to heat or cool the product being held in the product chambers. The heat transfer fluid preferably is recirculated through a chiller or heater. The heat transfer fluid facilitates freezing a product, keeping a product frozen and/or drying the product.

The present invention encompasses a wide variety in the numbers and the arrangements of the product chambers, the vacuum chambers, and the heat transfer chambers. For example, in one embodiment, the porous walls and the solid walls are arranged as substantially concentric cylinders such that every second chamber is a product chamber, every fourth chamber is a vacuum chamber, and all other chambers (also every fourth chamber) are heat transfer chambers. In another embodiment, every third chamber is a product chamber, every third chamber is a vacuum chamber, and every third chamber is a heat transfer chamber. In the foregoing embodiments, the innermost chamber may be a heat transfer chamber, a vacuum chamber, or a product chamber. In yet another embodiment, the solid walls and the porous walls are parallel to one another such that the chambers each have a rectangular cross section and are arranged in one of the same patterns as the previously described embodiments. In another embodiment, the walls separating the chambers are arranged in a grid, with each chamber having a rectangular cross section. In every second row, the chambers alternate between heat transfer chambers and product chambers. In every other row, the chambers alternate between product chambers and vacuum chambers.

In a preferred embodiment, the product chambers are no more than five inches in width, such that a product placed in the product chamber will be no more than five inches from a vacuum chamber and no more than five inches from a heat transfer chamber. More preferably, the product chambers are no more than one inch in width. These dimensions are optimal for facilitating vacuum and heat penetration of a frozen slurry or suspension.

In an embodiment of the invention, the apparatus further comprises a flange coupled to the container to facilitate inserting the product into and harvesting the product from the product chambers. In a preferred embodiment, the flange has a funnel shape with a wide opening attached to the top of the container and a narrow opening at the other end of the flange. The flange serves as a conduit for filling the product chambers with product and for harvesting filtered and dried product from the product chambers. In addition, the flange may include an end cap for sealing the container during the drying process. In another embodiment, the flange can have any other suitable shape.

In another embodiment, the apparatus further comprises a spout coupled to the flange so that a drug suspension may be sprayed directly into the product chambers. The spout comprises a tube for insertion into the flange, a fitting for attaching to the top of the flange, and a vent for allowing carrying fluid to boil off during insertion of the product into the container.

In another embodiment, the apparatus further comprises a control valve coupled to the vacuum chambers for streaming dry nitrogen gas into the vacuum chambers while the product is being dried under vacuum pressure. Because the pressure tends to decrease as the product is dried under vacuum pressure, streaming in nitrogen gas maintains a substantially constant pressure inside the vacuum chambers. In a preferred embodiment, the opening of the control valve is controlled by a programmed logic controller that is coupled to a pressure transmitter inside the container.

In another embodiment, the apparatus of the present invention comprises a container having a plurality of substantially concentric walls dividing the container into a plurality of chambers. The chambers and walls are numbered from 1 to n, counting from the innermost to the outermost, so that the chambers and walls are arranged according to the following pattern:
   if $(n+3)/4$ is a whole number then the wall with that number is a solid wall and the chamber surrounded by that wall is a heat transfer chamber;
   if $(n+2)/4$ is a whole number then the wall with that number is a porous wall and the chamber surrounded by that wall is a product chamber;
   if $(n+1)/4$ is a whole number, then the wall with that number is a porous wall and the chamber surrounded by that wall is a vacuum chamber; and,
   if $n/4$ is a whole number, then the wall with that number is a solid wall and the chamber surrounded by that wall is a product chamber.

In another embodiment, the chambers and walls are numbered from 1 to n, counting from the innermost to the outermost, so that the chambers and walls are arranged according to the following pattern:
   if $(n+3)/4$ is a whole number, then the wall with that number is a porous wall and the chamber surrounded by that wall is a vacuum chamber; and,
   if $(n+2)/4$ is a whole number then the wall with that number is a solid wall and the chamber surrounded by that wall is a product chamber;
   if $(n+1)/4$ is a whole number then the wall with that number is a solid wall and the chamber surrounded by that wall is a heat transfer chamber;
   if $n/4$ is a whole number, then the wall with that number is a porous wall and the chamber surrounded by that wall is a product chamber.

In yet another embodiment, the chambers and walls are numbered from 1 to n, counting from the innermost to the outermost, so that the chambers and walls are arranged according to the following pattern:
   if $(n+2)/3$ is a whole number then the wall with that number is a solid wall and the chamber surrounded by that wall is a heat transfer chamber;
   if $(n+1)/3$ is a whole number then the wall with that number is a porous wall and the chamber surrounded by that wall is a product chamber;
   if $n/3$ is a whole number, then the wall with that number is a solid wall and the chamber surrounded by that wall is a vacuum chamber.

In yet another embodiment, the apparatus of the present invention comprises a product chamber configured to hold a product, a vacuum source and a heat transfer source, such that the vacuum source and the heat transfer source are each located within five inches, and preferably within one inch, of all points within the product chamber. In another embodiment, the product chamber is no more than five inches, and preferably no more than one inch, in width.

The present invention also relates to a method of filtering and drying a product. An embodiment of the method comprises delivering a product to be filtered and dried into a product chamber that shares a porous wall with a vacuum chamber; filtering a substance from the product through the porous wall of the vacuum chamber; and drying the product by reducing the pressure in the vacuum chamber and in the product chamber.

According to an embodiment of the method, the product is filtered by allowing a substance to drain or filter through the porous walls of the product chambers. The filtration can be enhanced by actuating a vacuum pump coupled to the vacuum chamber. In an embodiment of the present invention, the product is dried by actuating the vacuum pump to reduce the pressure inside of the vacuum chambers and the product chambers, which causes the moisture to evaporate or sublime from the product and be condensed and frozen inside the condenser.

In another embodiment of the method of the present invention, a heat transfer fluid may flow through a heat transfer chamber that shares a solid wall with the product chamber. The heat transfer fluid preferably freezes the product, keeps the product frozen, or enhances the drying of the product.

According to the method of the present invention, the filtering and drying steps may be performed in any order or simultaneously and as many times as necessary to filter and dry the product. An embodiment of the method encompasses streaming dry nitrogen gas into the vacuum chamber during drying. After the product has been filtered and dried, the method preferably further encompasses harvesting the product by inverting the product chamber. This step may further include vibrating and/or rotating the product chamber.

Advantages of the Invention

One advantage of the present invention is that a product can be filtered and dried while holding the product in a single product chamber. This is a significant advantage over conventional freeze dryers, in which drying and filtration must be carried out in separate containers. Thus, the product does not need to be transferred as often, which reduces spillage or other errors, and increases the efficiency of the product manufacturing process.

A related advantage of the present invention is that secondary containers are not needed to hold a product inside of a drying chamber. By eliminating the use of secondary containers, the present invention may decrease yield losses on account of transferring the product between containers. Also, the product may be tightly packed within the product chambers, providing intimate contact with both the heat transfer chambers and the vacuum chambers.

Another advantage of the present invention is that all parts of the product chamber preferably are located less than five inches, and preferably less than one inch, from both a heat transfer chamber and a vacuum chamber. These distances are the most efficient for heat conduction and vacuum penetration through frozen suspensions, which leads to faster and more uniform drying than a conventional dryer.

Yet another advantage of the present invention is the configuration of the product chambers, the vacuum chambers, and the heat transfer chambers, so that a product chamber is preferably adjacent to a vacuum chamber and to a heat transfer chamber. This allows the dryer to have a compact shape and facilitates more efficient filtering and drying of the product. This design also maximizes the surface area of the product that can be exposed to the heat transfer chamber and to the vacuum chamber.

Another advantage of the present invention is that the dried product can be easily harvested directly from the product chambers through a flange, which acts as a funnel. This aspect of the present invention allows the product to be easily removed from the product chambers and transferred to another container while reducing or eliminating spillage.

Yet another advantage of the present invention is that the apparatus can be set up with sterile connections so that the product can be inserted, filtered, dried, and filtered without being exposed to the outside atmosphere. This advantage facilitates implementation of a quality system for the manufacture of the product. To that end, the entire dryer also can be cleaned and sterilized in place by flooding it with a clean-in-place (CIP) solution and by steaming it in place (SIP).

BRIEF DESCRIPTION OF THE DRAWINGS

The present invention is described with reference to the accompanying drawings. In the drawings, like reference numbers indicate identical or functionally similar elements. Additionally, the left-most digit of a reference number identifies the drawing in which the reference number first appears.

DETAILED DESCRIPTION OF THE PREFERRED EMBODIMENTS

Figure 1:
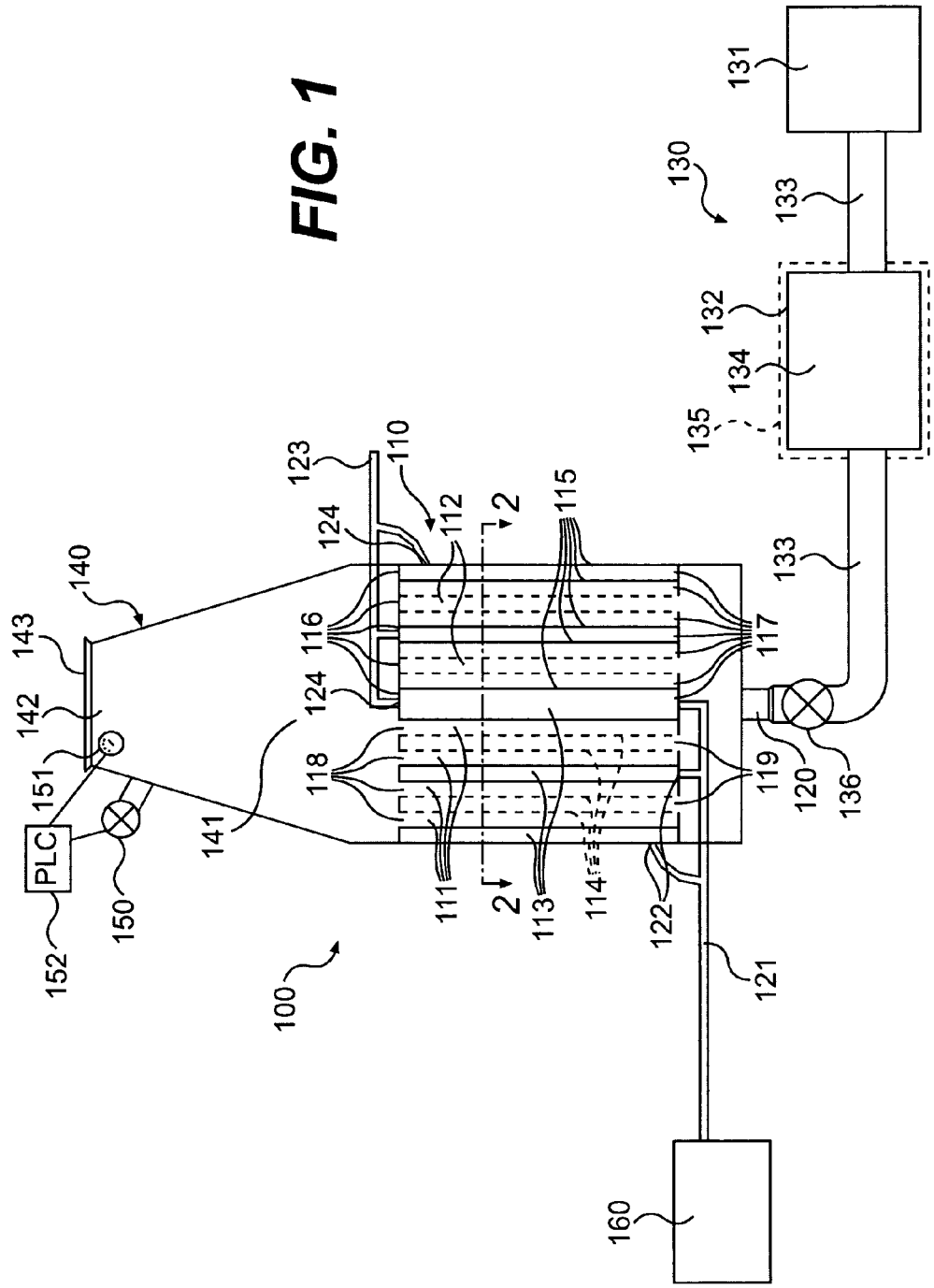
FIG. 1 is a sectional side view of a preferred embodiment of the apparatus for filtering and drying a product according to the present invention.

The present invention relates to a method and apparatus for filtering and drying a product. The preferred embodiments of the invention, described in detail in this section, relate to a method and apparatus for filtering and freeze drying a frozen drug suspension to form a dry, inhalable powder, or a dry friable powder, suitable for use as a medicament. However, it should be apparent that the present invention encompasses a method and apparatus for filtering and drying any type of product and is not limited to the preferred embodiments of the invention described below.

Preferred Embodiment of the Apparatus

An exemplary embodiment of the apparatus of the present invention will now be described. Referring to FIG. 1, an apparatus for filtering and drying 100 is shown. As illustrated in FIG. 1, apparatus 100 comprises a container 110 that contains a plurality of porous walls 114 (indicated by broken lines) and a plurality of solid walls 115 (indicated by solid lines) that divide the container into a plurality of product chambers 111, a plurality of vacuum chambers 112, and a plurality of heat transfer chambers 113. As shown in the embodiment of FIG. 1, each product chamber 111 is adjacent both to a vacuum chamber 112 and to a heat transfer chamber 113.

Each product chamber 111 is partially defined by a porous wall 114 that the product chamber shares with a vacuum chamber 112, and is partially defined by a solid wall 115 that the product chamber shares with a heat transfer chamber 113. In the embodiment shown in FIG. 1, each product chamber 111 also has a solid bottom 117 and an open top 118.

Each vacuum chamber 112 is partially defined by a porous wall 114 that the vacuum chamber 112 shares with an adjacent product chamber 111 and is partially defined by another porous wall 114 that the vacuum chamber 112 shares with another adjacent product chamber 111. Each vacuum chamber also has a solid top 116 and an open bottom 119, which is in communication with a vacuum port 120 at the base of the container 110. In the exemplary embodiment, vacuum port 120 comprises a two-inch diameter tri-clamp ferrule welded to the bottom of the container, although the vacuum port preferably has a larger diameter (about six inches) to facilitate faster drying of the product.

Each heat transfer chamber 113 is at least partially defined by a solid wall 115 that the heat transfer chamber 113 shares with an adjacent product chamber 111. Some of the heat transfer chambers are partially defined by another solid wall 115 that the heat transfer chamber 113 shares with another adjacent product chamber 111. Each heat transfer chamber 113 also has a solid top 116 and a solid bottom 117. Each heat transfer chamber is completely enclosed. In addition, each heat transfer chamber 113 is coupled to a heat transfer inlet 121, the heat transfer inlet being in communication with the heat transfer chamber via an inlet aperture 122. Each heat transfer chamber 113 is also coupled to a heat transfer outlet 123, the heat transfer outlet being in communication with the heat transfer chamber via an outlet aperture 124. The present invention may further comprise a heater or chiller 160 coupled to the heat transfer inlet and outlet for heating or cooling the heat transfer fluid as it is recirculated to and from the heat transfer chambers. The present invention also encompasses multiple heat transfer inlets or multiple heat transfer outlets of various configurations, as would be apparent to one of ordinary skill in the art.

FIGS. 2A–2D show cross-sectional views, along line 2—2 in FIG. 1, of four exemplary configurations of product chambers 111, vacuum chambers 112, and heat transfer chambers 113 in container 110 of the present invention. FIG. 3 shows another exemplary configuration of the product chambers 111, vacuum chambers 112, and heat transfer chambers 113 in container 110 of the present invention. It should be understood that these container configurations are presented as examples and the invention is not limited to the configurations discussed herein. The present invention encompasses other configurations of container 110 wherein a product chamber preferably shares a porous wall with a vacuum chamber.

Figure 2A:
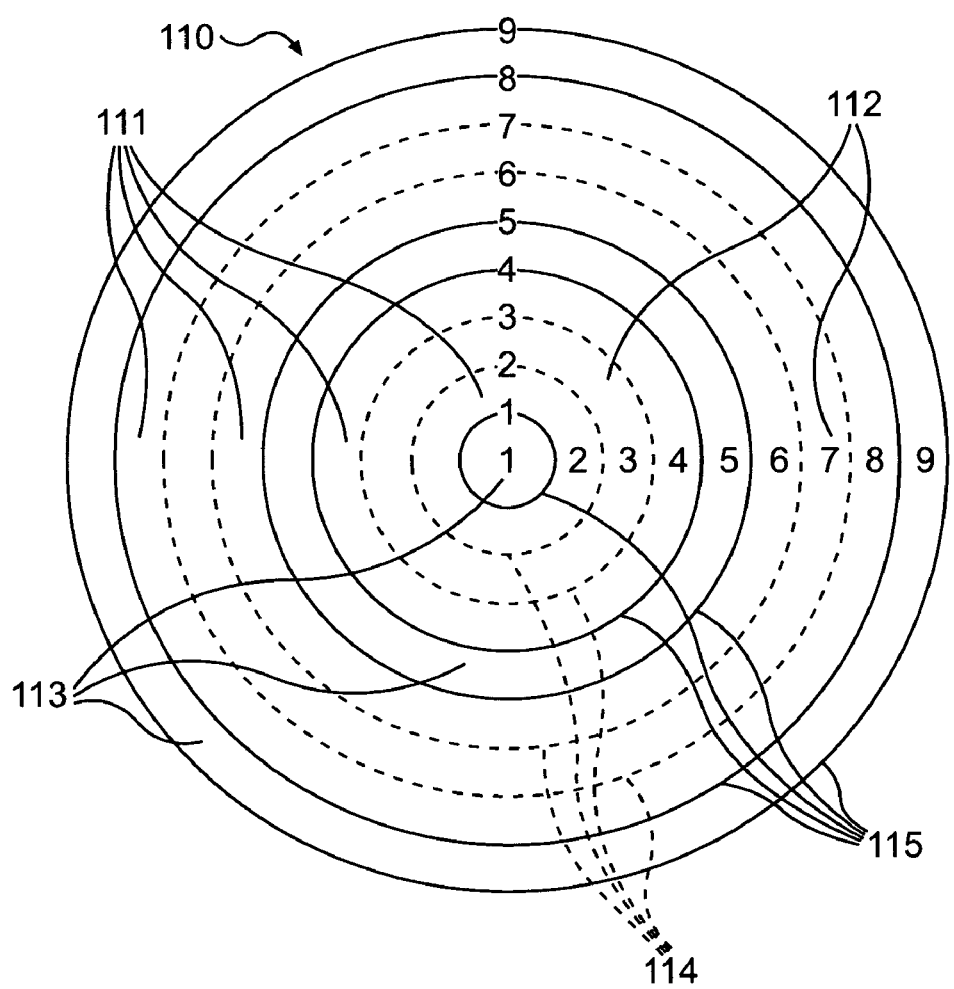
FIG. 2A is a cross sectional view along line 2—2 of FIG. 1, showing an embodiment of the container according to the present invention.
Figure 2B:
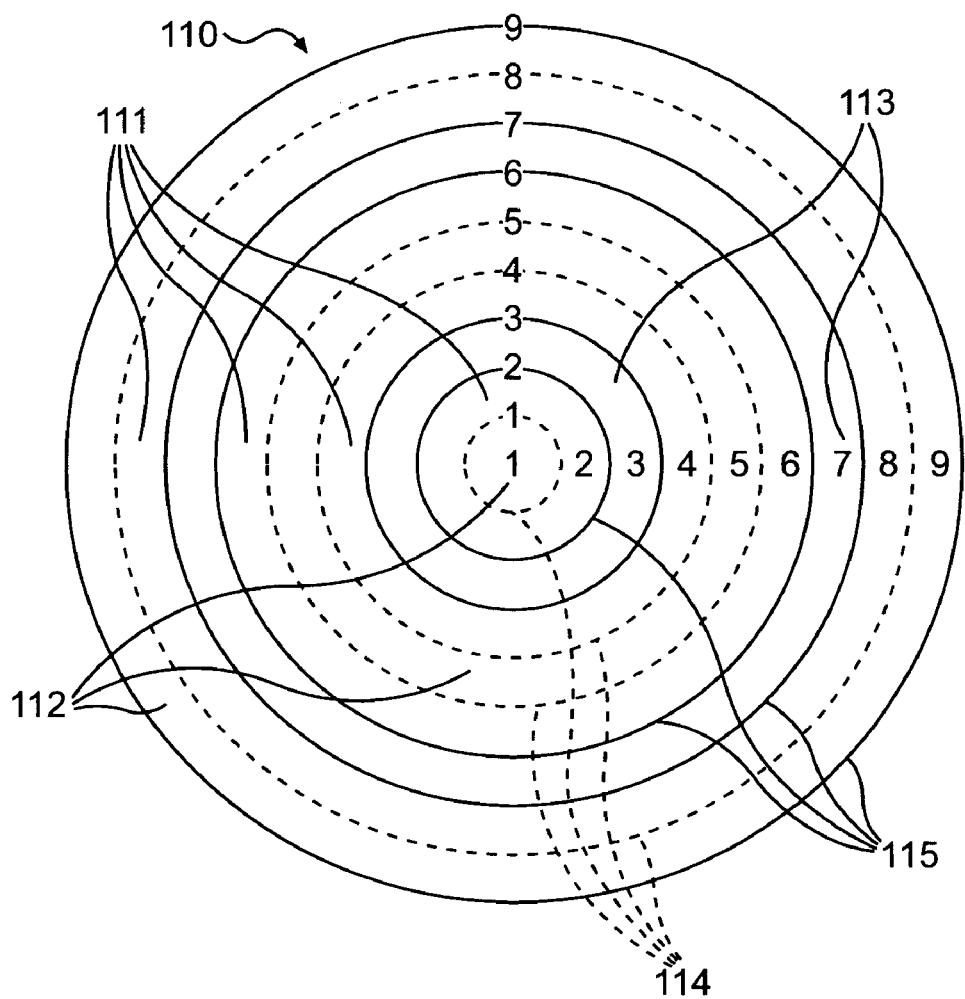
FIG. 2B is a cross sectional view along line 2—2 of FIG. 1, showing another embodiment of the container according to the present invention.
Figure 3:
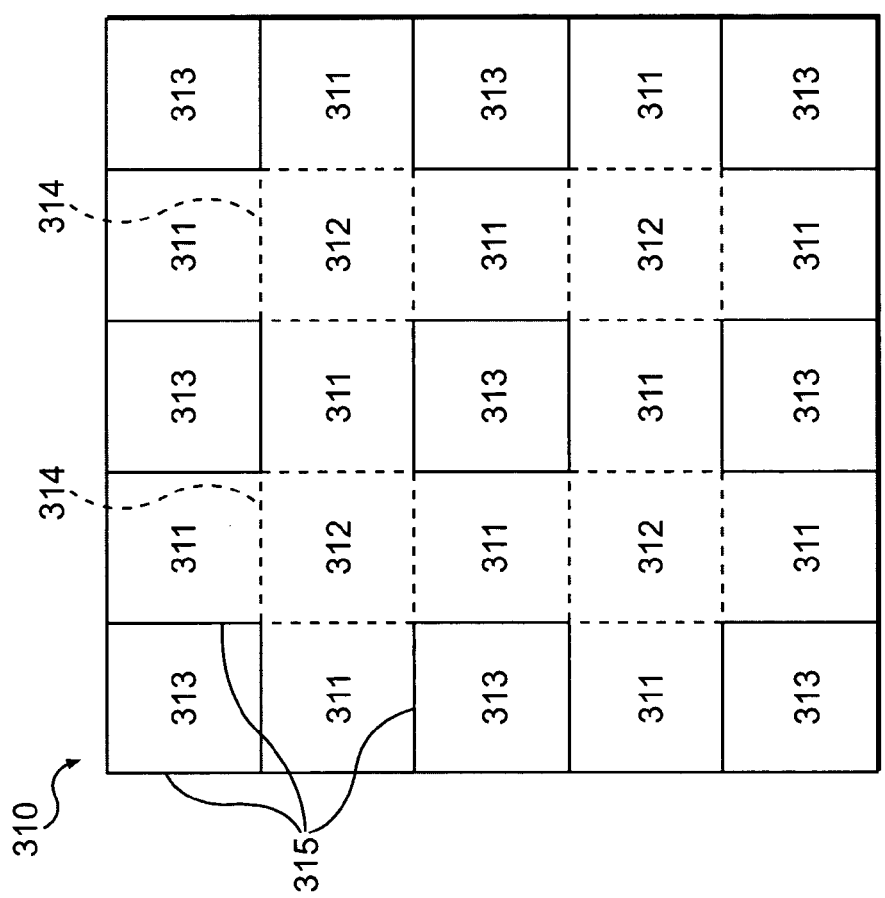
FIG. 3 is a cross sectional view showing yet another embodiment of the container according to the present invention.

FIGS. 2A and 2B illustrate two configurations of the chambers in which porous walls 114 and solid walls 115 are arranged as concentric cylinders that define product chambers 111, vacuum chambers 112, and heat transfer chambers 113. As shown in FIGS. 2A and 2B every second chamber is a product chamber 111, every fourth chamber is a vacuum chamber 112, and all other chambers (also every fourth chamber) are heat transfer chambers 113. It should be apparent that every product chamber 111 shares a porous wall 114 with a vacuum chamber 112 and shares a solid wall 115 with a heat transfer chamber 113. In the embodiment shown in FIG. 2A, the innermost chamber is a heat transfer chamber 113. In the embodiment shown in FIG. 2B, the innermost chamber is a vacuum chamber 112. Although not shown, this embodiment of the invention also encompasses the innermost chamber being a product chamber and other patterns of arrangement of the chambers.

As shown in FIG. 2A, if each of the walls 114, 115 and each of the chambers 111, 112, 113 is assigned a number from 1 to n, counting consecutively from the innermost wall and innermost chamber to the outermost wall and outermost chamber (see numbers 1–9 on FIG. 2A), the walls 114, 115 and the chambers 111, 112, 113 are arranged according to the following pattern:
  if (n+3)/4 is a whole number then the wall with that number is a solid wall 115 and the chamber surrounded by that wall is a heat transfer chamber 113;
  if (n+2)/4 is a whole number then the wall with that number is a porous wall 114 and the chamber surrounded by that wall is a product chamber 111;
  if (n+1)/4 is a whole number, then the wall with that number is a porous wall 114 and the chamber surrounded by that wall is a vacuum chamber 112; and
  if n/4 is a whole number, then the wall with that number is a solid wall 115 and the chamber surrounded by that wall is a product chamber 111.

FIG. 2A shows a preferred embodiment of this pattern of chambers wherein container 110 has nine chambers and the innermost chamber and the outermost chamber are both heat transfer chambers 113. Having the innermost chamber and outermost chamber be heat transfer chambers 113 helps maintain product chambers 111 at a uniform temperature.

As shown in FIG. 2B, if each of the walls 114, 115 and each of the chambers 111, 112, 113 is assigned a number from 1 to n, counting consecutively from the innermost wall and innermost chamber to the outermost wall and outermost chamber (see numbers 1–9 on FIG. 2B), the walls 114, 115 and the chambers 111, 112, 113 are arranged according to the following pattern:
  if (n+3)/4 is a whole number, then the wall with that number is a porous wall 114 and the chamber surrounded by that wall is a vacuum chamber 112; and,
  if (n+2)/4 is a whole number then the wall with that number is a solid wall 115 and the chamber surrounded by that wall is a product chamber 111;
  if (n+1)/4 is a whole number then the wall with that number is a solid wall 115 and the chamber surrounded by that wall is a heat transfer chamber 113;
  if n/4 is a whole number, then the wall with that number is a porous wall 114 and the chamber surrounded by that wall is a product chamber.

FIG. 2B shows a preferred embodiment of this pattern of chambers wherein container 110 has nine chambers and the innermost chamber and the outermost chamber are both vacuum chambers 112.

Figure 2C:
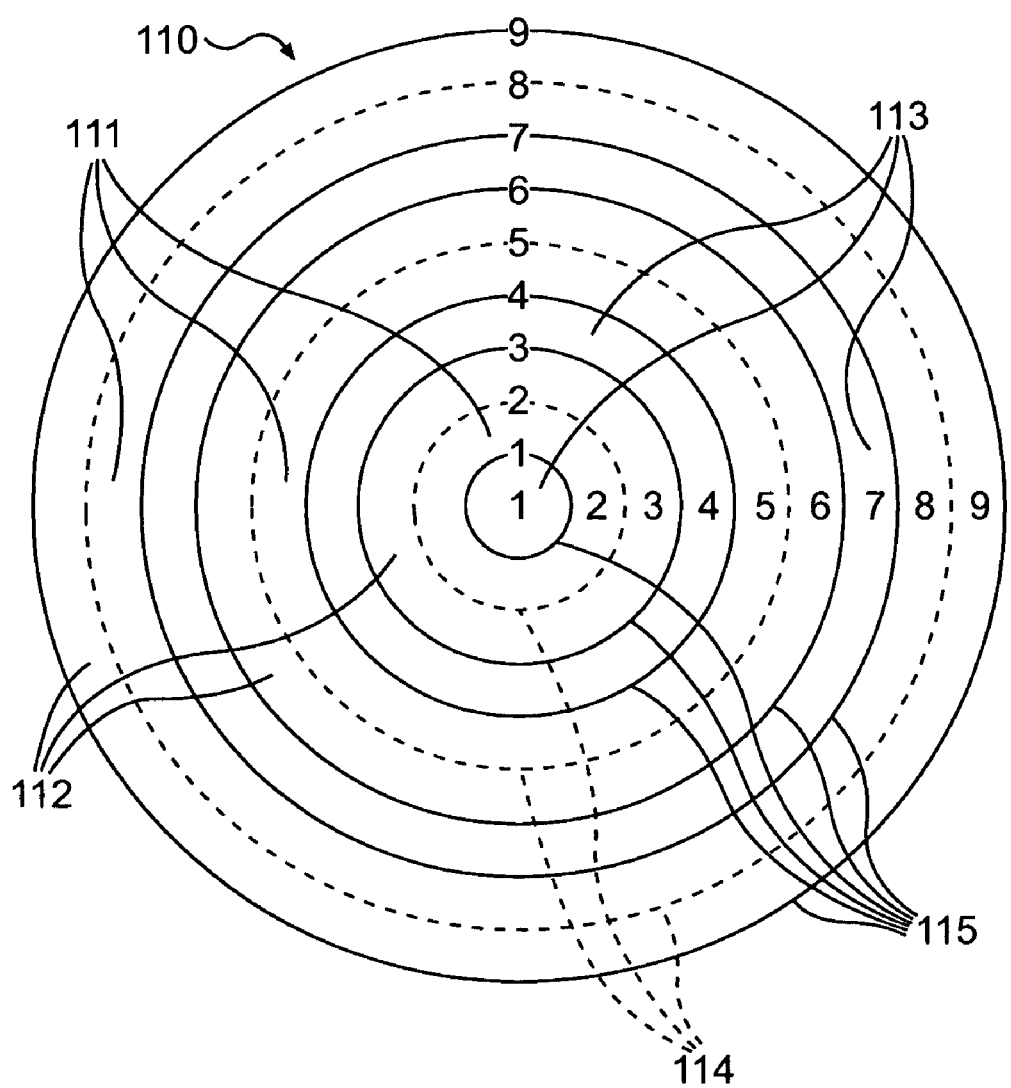
FIG. 2C is a cross sectional view along line 2—2 of FIG. 1, showing another embodiment of the container according to the present invention.

FIG. 2C illustrates another configuration of the chambers in which porous walls 114 and solid walls 115 are arranged as concentric cylinders that define product chambers 111, vacuum chambers 112, and heat transfer chambers 113. As shown in FIG. 2C every third chamber is a product chamber 111, every third chamber is a vacuum chamber 112, and every third chamber is a heat transfer chamber 113. It should be apparent that every product chamber 111 shares a porous wall 114 with a vacuum chamber 112 and shares a solid wall 115 with a heat transfer chamber 113. In the embodiment shown in FIG. 2C, the innermost chamber is a heat transfer chamber 113, although it should be understood that the innermost chamber may be a vacuum chamber 112 or a product chamber 111. As shown in FIG. 2C, if each of the walls 114, 115 and each of the chambers 111, 112, 113 is assigned a number from 1 to n, counting consecutively from the innermost wall and innermost chamber to the outermost wall and outermost chamber (see numbers 1–9 on FIG. 2C), the walls 114, 115 and the chambers 111, 112, 113 are arranged according to the following pattern:
  if (n+2)/3 is a whole number then the wall with that number is a solid wall and the chamber surrounded by that wall is a heat transfer chamber;
  if (n+1)/3 is a whole number then the wall with that number is a porous wall and the chamber surrounded by that wall is a product chamber;
  if n/3 is a whole number, then the wall with that number is a solid wall and the chamber surrounded by that wall is a vacuum chamber.

FIG. 2C shows a preferred embodiment of this pattern of chambers wherein container 110 has nine chambers. The present invention also encompasses variations on the shapes of the porous walls and solid walls shown in FIGS. 2A–2C. For example, the present invention encompasses porous walls and solid walls that have elliptical or rectangular cross sections or that have cross sections that are not concentric.

Figure 2D:
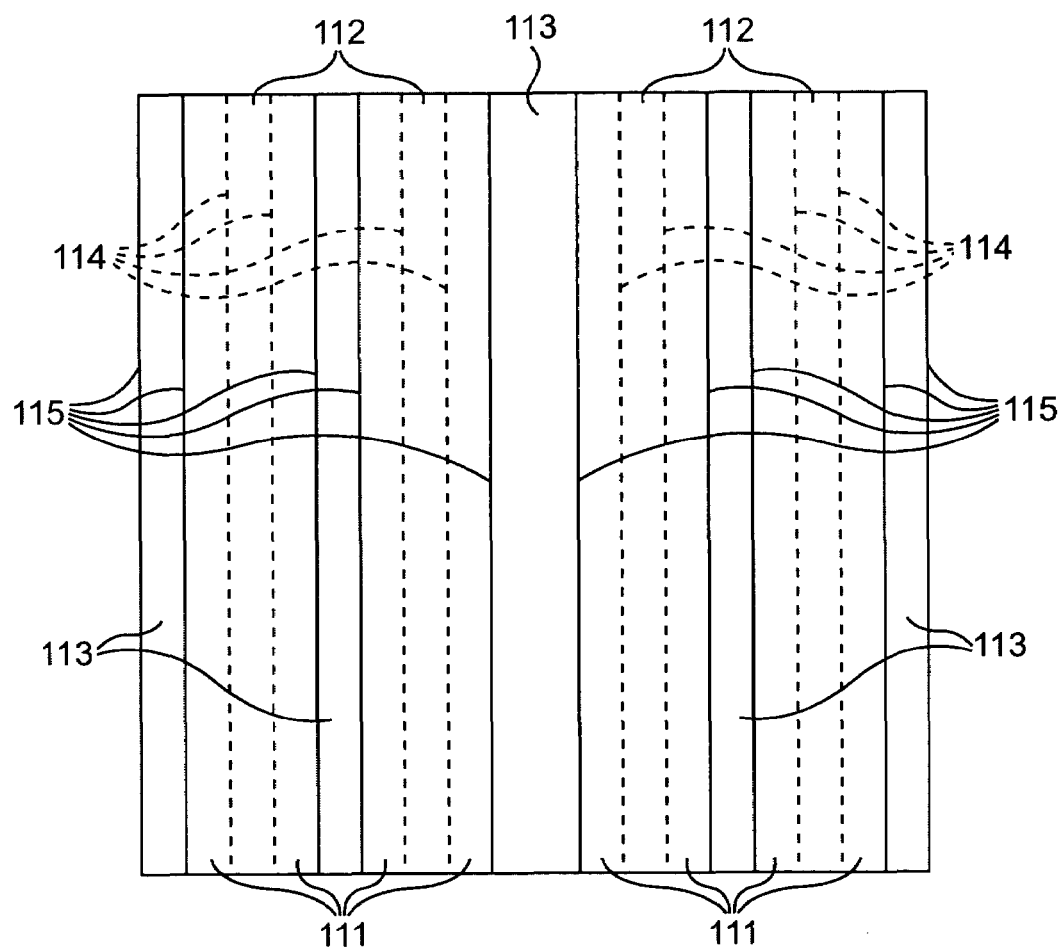
FIG. 2D is a cross sectional view along line 2—2 of FIG. 1, showing another embodiment of the container according to the present invention.

FIG. 2D shows a cross sectional view along line 2—2 in FIG. 1, depicting an alternative embodiment of the arrangement of chambers inside of the container according to the present invention. As shown in FIG. 2D, the porous walls 114 and the solid walls 115 are straight and parallel to one another (i.e. all of the porous walls are parallel to all of the solid walls), such that each of the chambers 111, 112, 113 has a rectangular cross-section. As in the arrangement depicted in FIG. 2A, every second chamber is a product chamber 111, every fourth chamber is a vacuum chamber 112, and all other chambers (also every fourth chamber) are heat transfer chambers 113, although it should be understood that the chambers can be arranged in any of the patterns discussed above. Also, every product chamber 111 shares a porous wall 114 with one vacuum chamber 112 and shares a solid wall with one heat transfer chamber 113.

FIG. 3 shows, in cross section, another embodiment of the arrangement of the chambers inside of a container 310 according to the present invention. As shown in FIG. 3, porous walls 314 (indicated by dashed lines) and solid walls 315 (indicated by solid lines) are arranged in a grid that define product chambers 311, vacuum chambers 312, and heat transfer chambers 313, each having a rectangular cross section. Every product chamber 311 shares at least one porous wall 314 with at least one vacuum chamber 312 and at least one solid wall 313 with at least one heat transfer chamber 315. In every second row of the grid, the chambers alternate between product chambers 311 and vacuum chambers 312. In every other row, the chambers alternate between heat transfer chambers 313 and product chambers 311. The present invention also encompasses other types of grid configurations not depicted in FIG. 3.

In any of the above embodiments, the arrangement of the chambers within the container gives the container a compact design, In addition, in a preferred embodiment of the invention, each product chamber is no more than five inches, and preferably no more than one inch, in width, which facilitates optimal penetration of vacuum and heat into the product chambers.

Solid walls 115 of the present invention are made of any solid material that has suitable strength and heat conductivity, for example stainless steel. Porous walls 114 are made of any material that has suitable strength and that has a pore size that is less than the particle size of the product to be filtered and dried. In one embodiment, the pore size is less than the particle size of at least 50% of the product to be filtered and dried. In a preferred embodiment, the pore size is less than the particle size of nearly all (i.e., at least approximately 90%) of the product to be filtered and dried. In one preferred embodiment, the pore size is less than the particle size of at least 99% of the product. Examples of suitable materials for porous walls 114 include sintered stainless steel, ceramic, plastic, and screen laminate. In a preferred embodiment of the invention illustrated in FIG. 1, porous walls 114 are made of sintered stainless steel having a pore size less than 20 μm in diameter. In a frozen suspension of a drug powder made according to the PPP, the drug particles are unlikely to be smaller than 20 μm in diameter. This pore size minimizes particle loss and maximizes product yield, at greater than 99%, without limiting the drainage of $LN_2$.

As shown in FIG. 1, the invention further comprises a vacuum 130 coupled to vacuum port 120, whereby vacuum 130 is in communication with each of the vacuum chambers 112. Vacuum 130 comprises a vacuum pump 131 coupled to vacuum port 120 via a condenser 132, vacuum tubes 133, and a vacuum valve 136. Vacuum pump 131 can be any well known vacuum pump that has the ability to reduce the pressure in a space. In an exemplary embodiment, condenser 132 comprises a microsphere process (MSP) extraction tank 134 surrounded by a cooling jacket 135 that can be filled with a coolant such as liquid nitrogen. Vacuum tubes 133 are any well known tubes that are able to withstand wide variations in temperature and pressure. In the exemplary embodiment, the vacuum tubes are two-inch diameter silicone vacuum hoses, although it would be preferable to use hard pipes with a larger diameter (about six inches) to facilitate lower pressures and faster drying. Vacuum valve 136 can be any valve well known in the art that is able to withstand extreme variations in temperature and pressure.

As shown in FIG. 1, the preferred embodiment of the invention further comprises a hollow flange 140 coupled to the top of the container 110. Flange 140 has a funnel shape having a circular cross section (not shown), with a wide opening 141 coupled to the top of the container 110 and a narrow opening 142 at the opposite end of the flange. In addition, flange 140 comprises a removable end cap 143 for sealing the container 110 to facilitate reducing the pressure in the vacuum chambers 112. Of course, the invention encompasses a wide variety of other shapes for the flange. For example, the flange could have a funnel shape with a narrow opening coupled to the top of the container and a wide opening located at the other end of the flange. In another alternative embodiment, the flange could have an elliptical or a rectangular cross section. The present invention encompasses any shape or size for the flange so long as it facilitates delivering the product into each of the product chambers. The flange also may serve as a conduit for removing the filtered and dried product from each of the product chambers.

Because the ability of vacuum pump 131 to decrease pressure increases as moisture is removed from the product, an embodiment of the invention further comprises a control valve 150 coupled to vacuum chambers 112 (preferably underneath end cap 143 of flange 140) for streaming a fluid into the vacuum chambers in order to keep the pressure in the vacuum chambers relatively constant. Control valve 150 also could be coupled to vacuum chambers 112 at other locations on container 110, such as in the space beneath vacuum chambers 112. In a preferred embodiment, a 5 psi tank of nitrogen gas (not shown) is coupled to control valve 150 upstream of vacuum chambers 112. The invention may further comprise a pressure transmitter 151 inside of the container 110 (preferably underneath end cap 143 of flange 140) coupled to a programmed logic controller (PLC) 152, which is coupled to control valve 150, so that the size of the opening of control valve 150 can be adjusted according to the pressure inside the container 110. For example, if the vacuum pump causes the pressure inside the vacuum chambers and the product chambers to drop below 525 mTorr, the PLC will open the valve to introduce nitrogen gas and raise the pressure inside the vacuum chambers to 525 mTorr.

Figure 4:
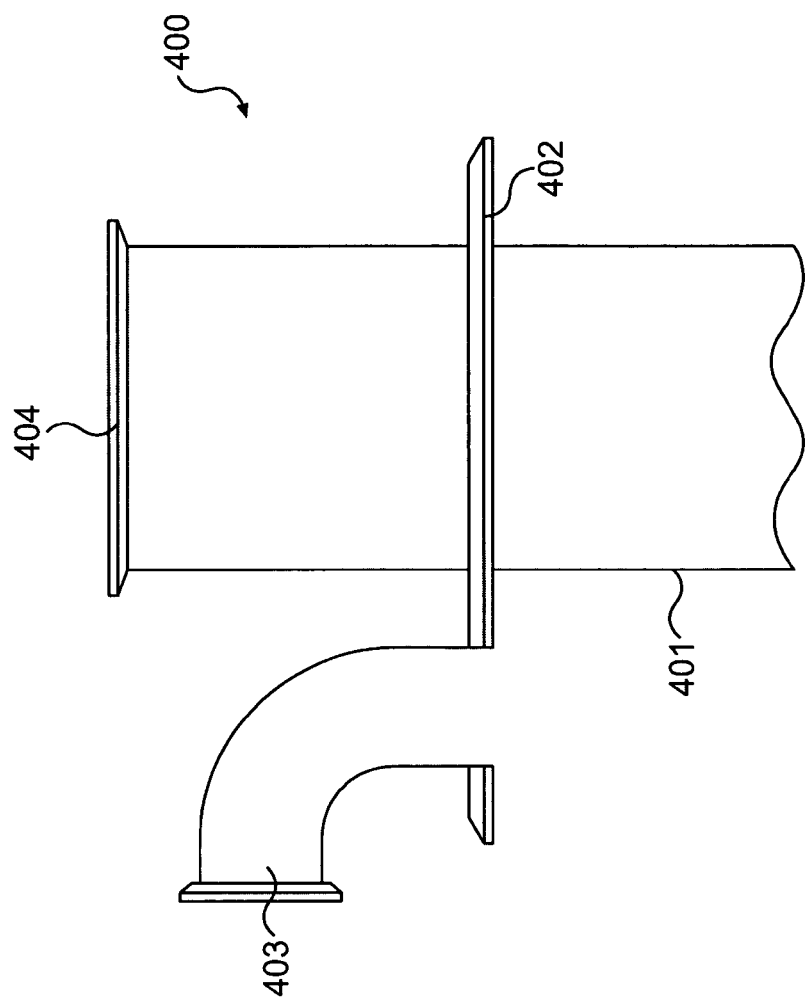
FIG. 4 is a side view of a preferred embodiment of a spout according to the present invention.

FIG. 4 depicts a spout 400 that is optionally coupled to narrow opening 142 at the top of flange 140 to facilitate filling of product chambers 111 by spraying the product directly into product chambers 111 with an atomizer (not shown), for example one used as part of the PPP. As shown in FIG. 4, spout 400 comprises a dip tube 401 to help carry frozen product into the product chambers 111, a fitting 402 for attachment to narrow opening 142 of flange 140 and a vent 403 for allowing excess carrying fluid to boil off of the product while it is being inserted into container 110. Spout 400 also has a connection 404 for forming a sterile seal with an atomizer, so that product chambers 111 may be spray-filled without exposing the product to the outside atmosphere.

Preferred Embodiment of the Method

The preferred embodiment of the method of the present invention will now be described in the context of explaining the operation of apparatus 100, as described above. A product to be filtered and dried is delivered into product chambers 111 through flange 140 and open tops 118 of product chambers 111. In an alternative embodiment, the product is delivered by spraying the product from an atomizer into product chambers 111 via spout 400 coupled to open top 142 of the flange. The present invention also encompasses other methods for introducing a product into the product chambers 111, such as pressure or vacuum assisted filling.

The product can be any product that needs to be filtered or dried. The product may be in any form, including in a suspension or a solution. In a preferred embodiment of the invention, the product is a frozen suspension of a drug. For example, the product could be a suspension of protein microspheres produced using the PPP, and kept frozen in a suspension of liquid nitrogen.

Once the product has been introduced into product chambers 111, the product is filtered and dried. The filtering step comprises removing a substance, such as excess carrying fluid or fine particles, from the product by allowing the substance to drain or filter through porous walls 114 of product chambers 111, into vacuum chambers 112, and out of container 110 via vacuum port 120 (or into vacuum 130 if it has been coupled to vacuum port 120). For example, after a slurry of frozen drug particles suspended in $LN_2$ is introduced into product chambers 111, the slurry is filtered by allowing the $LN_2$ to drain through porous walls 114, into vacuum chambers 112, and out of container 110 through vacuum port 120. In another embodiment, vacuum 130 could be coupled to vacuum chambers 112 during the filtering operation and vacuum pump 131 actuated to reduce the pressure inside vacuum chambers 112 to assist with filtration of the product. In yet another embodiment, a positive pressure may be applied inside product chambers 111 to assist with filtration of the product, such as by streaming additional dry nitrogen gas into the headspace above product chambers 111. In another embodiment, a brief, reverse flow of filtrate, such as liquid nitrogen, may be pumped into vacuum chambers 112, such as via vacuum port 120, in order to dislodge material that may have built up and be clogging porous walls 114 of product chambers 111.

The drying step comprises removing excess moisture from the product. The top opening of flange 140 is sealed with end cap 143 and vacuum 130 is attached to vacuum port 120. The pressure inside vacuum chambers 112 and product chambers 111 is reduced by actuating vacuum pump 131, which causes excess moisture to evaporate or sublime from the product. Condenser 132, which is located in-line between container 110 and vacuum pump 131, freezes and condenses fluid that evaporates or sublimes from the product. In a preferred embodiment of the invention, the drying operation comprises freeze-drying the product, in which the product remains frozen throughout the operation and the excess fluid sublimes from the product. According to a preferred embodiment of the apparatus, the product in each product chamber 111 is no more than five inches, and more preferably no more than one inch, from one of the vacuum chambers 112, as this distance is best suited for vacuum penetration through frozen suspensions.

In a preferred embodiment of the invention, the drying operation is performed by reducing the pressure inside vacuum chambers 112 and product chambers 111 to 30,000 mTorr or less, or more preferably to 525 mTorr or less. Because of the massive amount of fluid to be drained off of a frozen drug suspension made according to the PPP, it may take 20 hours or more for vacuum chambers 112 and product chambers 111 to reach this pressure. After that time, the pressure inside vacuum chambers 112 and product chambers 111 tends to decrease below the desired set point as the product is dried. Accordingly, the method of the present invention further comprises streaming dry nitrogen gas (or another gas) into the vacuum chambers through control valve 150 in order to keep the pressure in the vacuum chambers 112 and product chambers 111 constant, for example, at approximately 30,000 mTorr or 525 mTorr. In one embodiment of the invention, the amount of dry nitrogen gas streamed into vacuum chambers 112 is controlled by programmed logic controller (PLC) 152 coupled to pressure transmitter 151 inside vacuum chambers 112 to control the size of the opening in control valve 150.

In another embodiment of the method of the present invention, heat transfer fluid is pumped through heat transfer chambers 113 during the drying step. The heat transfer fluid can be used to cool the product to keep it frozen or to heat the product in product chambers 111 to offset the evaporative cooling effects of the sublimation of moisture from the product. Preferably, the heat transfer fluid is recirculated through chiller or heater 160. The heat transfer fluid can be any suitable fluid, including, for example, HFE-7100 (made by 3M Novec), water, steam, propylene glycol, or ethylene glycol. According to a preferred embodiment of the apparatus, the product in each product chamber 111 is no more than five inches, and preferably no more than one inch, from a heat transfer chamber 113 as this distance is best suited for heat penetration through frozen drug suspensions. In an alternative embodiment of the method of the present invention, the heat transfer fluid can be run cold in order to freeze a liquid product prior to drying it.

The invention encompasses varying the temperature of the heat transfer fluid. For example, in a preferred embodiment of the invention, the temperature of the heat transfer fluid is −40° C. when a product made according to the PPP process is delivered into product chambers 111, in order to keep the product frozen. During the drying process, the temperature of the heat transfer fluid gradually is increased to +25° C., as it has been found that this temperature profile best facilitates freeze-drying a drug powder made according to the PPP process. In another embodiment, the temperature of the heat transfer fluid could increase from −196° C. (the temperature of liquid nitrogen) to +25° C. for drying of solvent based products. In yet another embodiment, the temperature can be increased to greater than +25° C. in order to facilitate faster drying of the product.

In one embodiment of the invention, the filtering operation is performed before the drying operation. In another embodiment of the invention, the drying operation is performed before the filtering operation. In yet another embodiment of the invention, the filtering operation and the drying operation can be performed substantially simultaneously. According to the method of the present invention, either the filtering operation or the drying operation, or both, can be performed as many times as necessary to filter and dry the product. In another embodiment, the method of the present invention comprises rinsing the product after filtering or drying the product, after which additional steps of filtering and/or drying may be performed. After the product has been filtered and dried, the vacuum is relieved and the top end cap removed. By inverting container 110, the filtered and dried product can be removed and collected from product chambers 111. To facilitate removal of the product, container 110 also may be vibrated, such as by using a pneumatic vibrator (not shown), and/or rotated.

An advantage of the invention is that it facilitates sterile processing, which is critical in the manufacture of pharmaceutical products. For example, the apparatus 100 can be kept in an isolator (not shown), or inlet 142 of flange 140 and vacuum outlet 120 can be hooked up to sterile lines (not shown). In another aspect of the invention, the dryer may be cleaned and sanitized in place by flooding the container with clean-in-place (CIP) solution and by steaming it in place (SIP). The container can also be sterilized in place by steam.

Experiments

The following experiments further illustrate preferred embodiments of the apparatus and method of the present invention.

An apparatus for filtering and drying was constructed, having concentric cylindrical porous walls 114 and solid walls 115 dividing the container into product chambers 111, vacuum chambers 112, and heat transfer chambers 113, according to the embodiment shown in FIGS. 1 and 2A. The cylindrical porous walls 114 were made of sintered stainless steel with a pore size of less than 20 μm and the cylindrical solid walls 115 were made of solid stainless steel. The product chambers 111 have a total volume of 33 L. These dimensions were chosen so that the dryer could dry one batch (approximately 200 g) of drug, which has a wet volume of approximately 26 L.

Several preliminary tests were performed on the apparatus before attempting a drying experiment. Pressure tests of all of chambers 111, 112, 113 in container 110 confirmed that there were no leaks in the welds between walls 114, 115. Product chambers 111 were filled with liquid nitrogen, while vacuum valve 136 was closed, to ensure that product chambers 111 and vacuum chambers 112 could withstand cryogenic temperatures. Vacuum valve 136 was then opened and the liquid nitrogen drained out of product chambers 111 (through sintered stainless steel walls 114 and through vacuum chambers 112) within one minute, confirming the drainage and filtration abilities of the dryer. Vacuum chambers 112 and product chambers 111 were also tested to pressures as low as ~100 mTorr (at 25° C.). Upon releasing vacuum pump 131, the pressure rise was ~250 mTorr over 10 minutes, indicating a leak rate of ~3000 mTorr*L/minute (total volume of vacuum chambers 112 and product chambers 111 combined is ~120 L).

Several experimental trials were run with a frozen protein suspension of bovine serum albumin (BSA), made according to the PPP, as a model for human growth hormone (hGH) used to make the drug Nutropin®. In the PPP, a BSA-zinc complex, suspended in a salt water solution, was atomized into ~50 micron droplets and flash-frozen with liquid nitrogen.

In some trials, an atomizer sprayed these tiny frozen BSA particles (which look like snow) into buckets full of liquid nitrogen and then transferred from the bucket into product chambers 111 via flange 140. In other trials, an atomizer sprayed the BSA particles directly into product chambers 111 by attaching the atomizer to spout 400, which was coupled to the top of flange 140. Spraying directly into product chambers 111 eliminated the need for the buckets, minimized yield losses, and made it possible for apparatus 100 to function as a closed system.

The BSA microspheres filled the product chambers without mounding above open tops 118 of product chambers 111. In some cases, the BSA slurry did not fill the outer product chambers as completely as the inner product chambers. Pouring extra $LN_2$ around the outer product chambers helped the product fall into the outer product chambers. More uniform filling of the product chambers could be achieved, for example: by using an extra ring of $LN_2$ nozzles to fill the chambers; by making the outer product chambers lower in height than the inner product chambers, thereby causing the slurry to cascade into the outer product chambers; or by making the heat transfer chambers and vacuum chambers narrower in width, thereby increasing the percentage of cross sectional surface area open to product and giving the slurry less of a solid surface on which to accumulate.

Once the BSA suspension was inside product chambers 111, excess liquid nitrogen that had not already boiled off, was filtered through sintered stainless steel walls 114, into vacuum chambers 112, and out of container 110 through vacuum port 120 (vacuum 130 was not yet attached). When possible, a thermocouple (not shown) was placed into the frozen BSA suspension to monitor product temperature during the drying step. In addition, pressure transmitter 151 was attached to end cap 143, which was coupled to the top of flange 140. Vacuum 130 was attached to vacuum opening 120. Jacket 135 of condenser 132 was filled with $LN_2$ to create a cold surface on which water vapor that sublimed from the product could condense and freeze. Before opening vacuum valve 136, the pressure in condenser 134 was decreased to ~100 mTorr using vacuum pump 131.

From past experience with shelf freeze driers, it was known that freeze-drying a BSA suspension takes place under the following conditions: 525 mTorr and shelves holding the product at +25° C. It should be noted that the ice particles will remain frozen at these conditions, as evaporative cooling will keep the particles at −24° C. (which is the temperature corresponding to a vapor pressure of 525 mTorr for water), until they are dry. Once dry, the product will reach the shelf temperature of +25° C.

Thus, vacuum valve 136 was opened and vacuum pump 131 was actuated to reduce the pressure in vacuum chambers 112 and product chambers 111 to 525 mTorr or less. Because of the large amount of moisture in the BSA suspension and the small diameter (two inches) of vacuum tubing 131 and vacuum port 120, approximately 20 hours of drying elapsed before the pressure in vacuum chambers 112 and product chambers 111 reached 525 mTorr. Drying could be accelerated by using larger diameter vacuum tubing and a larger vacuum port, preferably at least six inches in diameter. After that time, for some of the trials, the pressure continued to drop until it reached 100 mTorr (the pressure inside of condenser 132). In other trials, control valve 150 was used to bleed nitrogen gas into vacuum chambers 112 to maintain the pressure as close to 525 mTorr as possible. In all of the trials, the temperature of the heat transfer fluid in heat transfer chambers 113 was increased from −40° C. to +25° C., in order to enhance the drying. Table I, below, summarizes the data from six experiments that were run at the above conditions.

TABLE I

| Lot # | Grams BSA | Drying cycle | Yield | Residual moisture (product spec < 8%) | % Drug (product spec 74–86%) |
|---|---|---|---|---|---|
| 01-31-88 | 200 | 2 days −4° C.; 1 day 10° C.; 3 days 25° C. | 90% | 3.78% | 80% |
| 01-27-160 | 200 | 4 days 25° C. | 89.5% | ND[1] | 81% |
| 01-27-202 | 200 | 4 days 25° C. | 92.2% | 6.7% | 82.3% |
| 01-57-15 | 250 | 4 days 25° C. | 90.3% | 7.8% | 80.6% |

TABLE I-continued

| Lot # | Grams BSA | Drying cycle | Yield | Residual moisture (product spec < 8%) | % Drug (product spec 74–86%) |
|---|---|---|---|---|---|
| 01-57-143 | 200 | 4 days 25° C. | 90.8% | ND[1] | ND |
| 02-10-50 | 100 | 4 days 25° C. | 85.8% | ND[1] | ND |

[1](ND = Not Determined) Although residual moisture has not been determined, the product is expected to be dry because there were no condenser failures and because the final particle size was <5 microns (it is known that BSA with residual moisture has larger particle sizes).

In another experiment, apparatus 100 was used to filter and dry microspheres of polylactic glycolic acid (PLGA), a biodegradable polymer that is used to encapsulate certain time-release drugs. First, frozen droplets of PLGA in acetonitrile were made by freezing and cryogenically milling PLGA. The PLGA in acetonitrile was suspended in liquid nitrogen and introduced into product chambers 111. Excess liquid nitrogen was filtered through sintered stainless steel porous walls 114. The PLGA droplets were freeze-dried to remove the acetonitrile by actuating vacuum pump 131 to reduce the pressure in vacuum chambers 112 and product chambers 111 to approximately 200 mTorr for three days. The heat transfer fluid was run at −25° C. for the first two days, at −10° C. for the third day and at +25° C. for one additional day before harvesting. About 75% of the PLGA was collected as dry, suitable powder. This process could be used to make PLGA particles containing a drug.

The apparatus also could be used to filter and dry polymer microspheres that are made via an emulsion process. The emulsion process produces solid microspheres suspended in a curing fluid, typically water or an oil. Usually, the microspheres are collected on a sieve, for filtering, and then dried by applying a vacuum, blowing air, applying heat, or some combination thereof. The apparatus of the present invention could be used to filter and dry the microspheres. The curing fluid could be filtered through the porous walls and the microspheres could be dried by reducing the pressure in the vacuum chambers and applying heat via the heat transfer chambers.

In addition, the apparatus could be used to filter and dry zinc carbonate particles suspended in salt water. First, a liquid suspension could be poured into product chambers 111. Next, the salt water would be filtered through sintered stainless steel porous walls 114, with residual salt being removed by repeated water rinses. After filtration was complete, the remaining zinc carbonate particles would be frozen by pumping very cold heat transfer solution through heat transfer chambers 113. Once the product was frozen, vacuum pump 131 could be actuated to reduce the pressure in vacuum chambers 112 and product chambers 111 to dry the product.

CONCLUSION

While various embodiments of the present invention have been described above, it should be understood that they have been presented by way of example only, and not limitation. For example, the present invention is not limited to the physical arrangements or dimensions illustrated or described. Nor is the present invention limited to any particular design or materials of construction. As such, the breadth and scope of the present invention should not be limited to any of the above-described exemplary embodiments, but should be defined only in accordance with the following claims and their equivalents.

We claim:

1. An apparatus for filtering and drying a product, the apparatus comprising:
   a first product chamber;
   a vacuum chamber;
   a first porous wall that at least partially defines the first product chamber and that at least partially defines the vacuum chamber;
   wherein the first product chamber is configured to hold the product for filtering through the first porous wall;
   further comprising a heat transfer chamber coupled to the first product chamber;
   further comprising a first solid wall at least partially defining the heat transfer chamber and at least partially defining the first product chamber; and
   wherein the distance between the first solid wall and the first porous wall is at most five inches.

2. The apparatus of claim 1, wherein the distance between the first solid wall and the first porous wall is at most one inch.

3. The apparatus of claim 1, wherein the first porous wall and the first solid wall are substantially concentric.

4. The apparatus of claim 3, wherein the distance between the first porous wall and the first solid wall is at most one inch.

5. An apparatus for filtering and drying a product, the apparatus comprising:
   a first product chamber;
   a vacuum chamber;
   a first porous wall that at least partially defines the first product chamber and that at least partially defines the vacuum chamber;
   wherein the first product chamber is configured to hold the product for filtering through the first porous wall;
   further comprising a second product chamber; and
   a second porous wall that at least partially defines the vacuum chamber and that at least partially defines the second product chamber.

6. An apparatus for drying and filtering a product, the apparatus comprising:
   a container comprising a plurality of porous walls and a plurality of solid walls separating the container into a plurality of product chambers, a plurality of vacuum chambers, and a plurality of heat transfer chambers;
   wherein each of the plurality of product chambers shares at least one of the plurality of porous walls with at least one of the plurality of vacuum chambers and each of the plurality of product chambers shares at least one of the plurality of solid walls with at least one of the plurality of heat transfer chambers.

7. The apparatus of claim 6, wherein:
   each wall separating one of the plurality of vacuum chambers and one of the plurality of product chambers is one of the plurality of porous walls;
   each wall separating one of the plurality of product chambers and one of the plurality of heat transfer chambers is one of the plurality of solid walls; and,
   each wall separating one of the plurality of heat transfer chambers and one of the plurality of vacuum chambers is one of the plurality of solid walls.

8. The apparatus of claim 6, further comprising a vacuum pump coupled to each of the plurality of vacuum chambers for reducing the pressure in the plurality of vacuum chambers.

9. The apparatus of claim 8, further comprising a condenser coupled to each of the plurality of vacuum chambers and to the vacuum pump.

10. The apparatus of claim 6, further comprising a control valve coupled to the plurality vacuum chambers for streaming fluid into the plurality of vacuum chambers.

11. The apparatus of claim 10, further comprising:
a pressure transmitter coupled to the container; and,
a programmed logic controller coupled to the pressure transmitter and to the control valve;
wherein the programmed logic controller controls the amount of fluid that streams through the control valve responsive to the pressure in the container.

12. The apparatus of claim 6, further comprising a heat transfer inlet coupled to the plurality of heat transfer chambers and a heat transfer outlet coupled to the plurality of heat transfer chambers.

13. The apparatus of claim 6, wherein each of the plurality of heat transfer chambers has a solid top and a solid bottom.

14. The apparatus of claim 6, wherein each of the plurality of product chambers has an open top and a solid bottom.

15. The apparatus of claim 6, wherein each of the plurality of vacuum chambers has a solid top and an open bottom.

16. The apparatus of claim 6, wherein the plurality of porous walls and the plurality of solid walls are substantially concentric.

17. The apparatus of claim 16, wherein the innermost wall is one of the plurality of solid walls and surrounds one of the plurality of heat transfer chambers.

18. The apparatus of claim 17, wherein the walls, other than the innermost wall, are arranged in alternating pairs of the plurality of porous walls and pairs of the plurality of solid walls, and wherein the innermost wall is adjacent to a porous wall.

19. The apparatus of claim 6, wherein every second chamber is one of the plurality of product chambers, every fourth chamber is one of the plurality of vacuum chambers, and all other chambers are heat transfer chambers.

20. The apparatus of claim 19, wherein one of the heat transfer chambers is the innermost chamber.

21. The apparatus of claim 19, wherein one of the vacuum chambers is the innermost chamber.

22. The apparatus of claim 6, wherein every third chamber is a product chamber, every third chamber is a heat transfer chamber, and every third chamber is a vacuum chamber.

23. The apparatus of claim 22, wherein one of the heat transfer chambers is the innermost chamber.

24. The apparatus of claim 22, wherein one of the vacuum chambers is the innermost chamber.

25. The apparatus of claim 6, wherein each of the plurality of product chambers, each of the plurality of vacuum chambers and each of the plurality of heat transfer chambers has a rectangular cross-section.

26. The apparatus of claim 6, wherein all of the plurality of porous walls are parallel to all of the plurality of solid walls.

27. The apparatus of claim 6, wherein the plurality of porous walls and the plurality of solid walls are arranged in a grid defining one or more rows of chambers.

28. The apparatus of claim 27, wherein in every other row of chambers, the chambers alternate between one of the plurality of heat transfer chambers and one of the plurality of product chambers.

29. The apparatus of claim 27, wherein in every other row of chambers, the chambers alternate between one of the plurality of product chambers and one of the plurality of vacuum chambers.

30. The apparatus of claim 6, wherein each of the plurality of product chambers has a width of less than five inches.

31. The apparatus of claim 6, wherein each of the plurality of product chambers has a width of less than one inch.

32. The apparatus of claim 6, further comprising a flange coupled to a top of the container for guiding the delivery of the product into the product chambers.

33. The apparatus of claim 32, further comprising a spout coupled to the flange for facilitating spraying the product into the product chambers.

34. The apparatus of claim 33, wherein the spout comprises a vent.

35. The apparatus of claim 6, wherein each porous wall comprises a material having a pore size that is smaller than a particle size of nearly all of the product.

36. The apparatus of claim 35, wherein the material comprises sintered stainless steel.

37. The apparatus of claim 35, wherein the material comprises ceramic.

38. The apparatus of claim 35, wherein the material comprises plastic.

39. The apparatus of claim 35, wherein the material comprises screen laminate.

40. The apparatus of claim 35, wherein the pore size is no greater than 20 µm.

41. An apparatus for filtering and drying a product, the apparatus comprising:
a container comprising a plurality of substantially concentric walls dividing the container into a plurality of chambers, wherein each chamber and each wall surrounding that chamber is assigned a number from 1 to n, counting consecutively from the innermost chamber and innermost wall to the outermost chamber and outermost wall, wherein
if $(n+3)/4$ is a whole number then the wall with that number is a solid wall and the chamber surrounded by that wall is a heat transfer chamber;
if $(n+2)/4$ is a whole number then the wall with that number is a porous wall and the chamber surrounded by that wall is a product chamber;
if $(n+1)/4$ is a whole number, then the wall with that number is a porous wall and the chamber surrounded by that wall is a vacuum chamber;
if $n/4$ is a whole number, then the wall with that number is a solid wall and the chamber surrounded by that wall is a product chamber.

42. The apparatus of claim 41, wherein n=9.

43. The apparatus of claim 41, wherein (n−1) is a multiple of 4.

44. An apparatus for filtering and drying a product, the apparatus comprising:
a container comprising a plurality of substantially concentric walls dividing the container into a plurality of chambers, wherein each chamber and each wall surrounding that chamber is assigned a number from 1 to n, counting consecutively from the innermost chamber and innermost wall to the outermost chamber and outermost wall, wherein
if $(n+3)/4$ is a whole number, then the wall with that number is a porous wall and the chamber surrounded by that wall is a vacuum chamber;
if $(n+2)/4$ is a whole number then the wall with that number is a solid wall and the chamber surrounded by that wall is a product chamber;
if $(n+1)/4$ is a whole number then the wall with that number is a solid wall and the chamber surrounded by that wall is a heat transfer chamber;

if n/4 is a whole number, then the wall with that number is a porous wall and the chamber surrounded by that wall is a product chamber.

45. The apparatus of claim 44, wherein n=11.

46. The apparatus of claim 44, wherein (n−3) is a multiple of 4.

47. An apparatus for filtering and drying a product, the apparatus comprising:
a container comprising a plurality of substantially concentric walls dividing the container into a plurality of chambers, wherein each chamber and each wall surrounding that chamber is assigned a number from 1 to n, counting consecutively from the innermost chamber and innermost wall to the outermost chamber and outermost wall, wherein
if (n+2)/3 is a whole number, then the wall with that number is a solid wall and the chamber surrounded by that wall is a heat transfer chamber;
if (n+1)/3 is a whole number then the wall with that number is a porous wall and the chamber surrounded by that wall is a product chamber;
if n/3 is a whole number then the wall with that number is a solid wall and the chamber surrounded by that wall is a vacuum chamber.

48. The apparatus of claim 47, wherein n=9.

49. The apparatus of claim 47, wherein n is a multiple of 3.

50. The apparatus of claim 43, wherein every point in the product chamber is no more than one inch from a point on the heat transfer source and no more than one inch from a point on the vacuum source.

51. A method of filtering and drying a product comprising the steps of:
providing a product chamber and a vacuum chamber, the product chamber and the vacuum chamber sharing a porous wall;
delivering a product into the product chamber;
filtering a substance from the product through the porous wall; and
drying the product;
wherein the product comprises fine frozen particles and the substance comprises liquid nitrogen.

52. A method of filtering and drying a product comprising the steps of:
providing a product chamber and a vacuum chamber, the product chamber and the vacuum chamber sharing a porous wall;
delivering a product into the product chamber;
filtering a substance from the product through the porous wall; and
drying the product;
wherein the product comprises polymer microspheres.

53. A method of filtering and drying a product comprising the steps of:
providing a product chamber and a vacuum chamber, the product chamber and the vacuum chamber sharing a porous wall;
delivering a product into the product chamber;
filtering a substance from the product through the porous wall; and
drying the product;
wherein the product comprises a protein.

54. A method of filtering and drying a product comprising the steps of:
providing a product chamber and a vacuum chamber, the product chamber and the vacuum chamber sharing a porous wall;
delivering a product into the product chamber;
filtering a substance from the product through the porous wall; and
drying the product;
wherein the product comprises a drug.

55. A product filtered and dried according to a method of filtering and drying a product comprising the steps of:
providing a product chamber and a vacuum chamber, the product chamber and the vacuum chamber sharing a porous wall;
delivering a product into the product chamber;
filtering a substance from the product through the porous wall; and
drying the product.

* * * * *